(12) United States Patent
Friedman et al.

(10) Patent No.: US 7,064,127 B2
(45) Date of Patent: Jun. 20, 2006

(54) TREATMENT OF HEPATIC FIBROSIS WITH IMATINIB MESYLATE

(75) Inventors: Scott Friedman, Scarsdale, NY (US); Efsevia Albanis, New York, NY (US)

(73) Assignee: Mount Sinai School of Medicine of New York University, New York, NY (US)

( * ) Notice: Subject to any disclaimer, the term of this patent is extended or adjusted under 35 U.S.C. 154(b) by 7 days.

(21) Appl. No.: 11/002,715

(22) Filed: Dec. 2, 2004

(65) Prior Publication Data

US 2005/0143389 A1 Jun. 30, 2005

Related U.S. Application Data

(60) Provisional application No. 60/531,252, filed on Dec. 19, 2003.

(51) Int. Cl.
*A61K 31/497* (2006.01)
(52) U.S. Cl. .................................. 514/252.18
(58) Field of Classification Search ............ 514/252.18
See application file for complete search history.

(56) References Cited

U.S. PATENT DOCUMENTS 6,872,715 B1    3/2005  Santi et al.
2003/0147813 A1 *  8/2003  Lyons ........................ 424/45
2003/0203846 A1 * 10/2003  Srivastava et al. ............ 514/12
2004/0121971 A1 *  6/2004  Chen et al. .................... 514/44
2005/0261283 A1 * 11/2005  Sukhatme ................ 514/222.5

OTHER PUBLICATIONS

Kinnman, Laboratory Investigation, vol. 83, No. 2, Feb. 2003, "The Myofibroblastic Conversion of Peribiliary Fibrogenic Cells Distinct from Hepatic Stellate Cells is Stimulated by Platelet-Derived Growth Factor During Liver Fibrogenesis", pp. 163-173.*

* cited by examiner

*Primary Examiner*—Raymond J. Henley, III
(74) *Attorney, Agent, or Firm*—Darby & Darby

(57) ABSTRACT

Disclosed herein is a method for treating hepatic fibrosis comprising administering to a patient in need of such treatment an amount effective to treat hepatic fibrosis of imatinib mesylate. This is based on the ability of imatinib mesylate to down regulate stellate cell activation in culture and in vivo. Hepatic fibrosis is not limited to patients with chronic Hepatitis B, Hepatitis C, non-alcoholic steatohepatitis (NASH), alcoholic liver disease, metabolic liver diseases (Wilson's disease, hemochromatosis), biliary obstruction (congenital or acquired) or liver diseases associated with fibrosis of unknown cause.

5 Claims, No Drawings

TREATMENT OF HEPATIC FIBROSIS WITH IMATINIB MESYLATE

FIELD OF THE INVENTION

The present invention is directed to methods of treating hepatic fibrosis in humans.

BACKGROUND OF THE INVENTION

Progressive fibrosis of liver often results in organ failure leading to death or the need for transplantation. These diseases affect hundreds of millions in the United States and worldwide [1]. For example, hepatic fibrosis is the leading non-malignant gastrointestinal cause of death in the United States. Moreover, it has been increasingly recognized that progression of fibrosis is the single most important determinant of morbidity and mortality in patients with chronic liver disease [2].

There has been remarkable progress in elucidating the cellular basis of fibrosis in liver, kidney and lung. In liver, activation of resident mesenchymal cells known as "stellate cells" is a key event [3]. Activation represents a transformation to a myofibroblast-like cell that is proliferative, fibrogenic and contractile. The extent of fibrosis is directly related to the numbers of these fibrogenic activated stellate cells.

It has been previously demonstrated that activation and proliferation of hepatic stellate cells (HSC) in liver injury is associated with de novo expression of many cytokine receptors, including beta platelet-derived growth factor receptor (β-PDGFR) [4]. β-PDGF receptor expression in injured liver is largely confined to these activated mesenchymal cells; the rare large arteries within the parenchyma are the only other site within the organ. Thus, the extent of β-PDGF receptor expression parallels the mass of activated stellate cells, which in turn reflects the extent of fibrosis. Moreover, reduction in fibrosis is accompanied by diminished numbers of such activated cells [5].

Recent advances in anti-inflammatory arid-anti-fibrotic therapies offers the prospect of delaying these outcomes, but to date there are no approved antifibrotic therapies, leaving hundreds of millions of patients worldwide who have chronic liver disease with no therapeutic options apart from the possibility of liver transplantation. Currently only a single trial of antifibrotic therapy is underway (gamma interferon), and the hepatology community and pharmaceutical sector anxiously await results from this trial, as several other putative antifibrotics agents are in development by a number of companies. There has been growing recognition and enthusiasm for the prospect of treating hepatic fibrosis [6]. Thus, there is a large untapped market that is highly receptive to this new approach to treating liver fibrosis.

The development of imatinib mesylate (GLEEVEC™) represented an important milestone in the treatment of chronic myelogenous leukemia (CML), since this small molecular inhibitor of the BCR-ABL oncogene product, the key molecular abnormality in this cancer, is remarkably safe and effective [7–9]. The drug is also effective in CML associated with rearrangements of the β-PDGF receptor [10]. Thus, thousands of patients have been safely treated with modest drug resistance reported. More recently, the drug has been approved for the treatment of GI Stromal tumors, mesenchymal cell neoplasms of the intestinal tract [11]. Of importance, this agent not only blocks the BCR-ABL receptor tyrosine kinase protein, but it has inhibitory activity across a number of related receptor tyrosine kinases, including β-PDGF receptor, a key mediator of stellate cell activation in hepatic fibrosis[12]. Indeed, a recent report has begun to examine the potential impact of GLEEVEC™ on hepatic fibrosis in a rodent model of bile duct obstruction, a standard model used in the field[13].

SUMMARY OF THE INVENTION

It has now been unexpectedly discovered that GLEEVEC™ can be used as a treatment for patients suffering from hepatic fibrosis based on its ability to down-regulate stellate cell activation in culture and in vivo. This includes but is not limited to patients with chronic Hepatitis B, Hepatitis C, non-alcoholic steatophepatitis (NASH), alcoholic liver disease, metabolic liver diseases (Wilson's disease, hemochromatosis), biliary obstruction (congenital or acquired) or liver diseases associated with fibrosis of unknown cause.

In one aspect, the present invention provides a method for treating hepatic fibrosis comprising administering to a patient in need of such treatment an amount effective to treat hepatic fibrosis of imatinib mesylate.

This and other aspects of the present invention will be apparent to those of ordinary skill in the art in light of the present specification and appended claims.

DETAILED DESCRIPTION OF THE INVENTION

In the discussions below, the term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

Presented below is an overview of the pathogenesis of hepatic fibrosis and the role of the activated hepatic stellate cell.

The hepatic scar consists of a broad accumulation of extracellular matrix (ECM), which includes the macromolecules that comprise the scaffolding of normal and fibrotic liver. These macromolecules consist of three main families: collagens, glycoproteins, and proteoglycans. As the normal liver becomes fibrotic, significant qualitative and quantitative changes occur in the ECM. The content of collagens and noncollagenous components increases three-to fivefold in cirrhotic compared with normal liver. Moreover, the type of subendothelial ECM shifts from low-density basement membrane-like matrix to an interstitial type, which is rich in type I, or fibrillar collagen.

HSCs and their related cell types (e.g., "myofibroblasts") are the major cellular source of hepatic ECM in the injured liver. HSCs are located in the subendothelial space of Disse between sinusoidal endothelium and hepatocytes (14). They represent a pericytic cell type with the potential for conversion to a "myofibroblast," similar to mesangial cells in the kidney, pulmonary mesenchymal cells, and stellate cells in the pancreas [17].

In liver injury of any type, HSCs undergo activation, which connotes the transition from a quiescent vitamin A-rich cell to a proliferative, highly fibrogenic, and contractile cell with reduced vitamin A content. HSC activation begins almost immediately after the onset of liver injury and progresses through a continuum of cellular and molecular events that can lead to sustained scar accumulation. Alternatively, resolution of fibrosis and loss of activated HSCs through reversion or apoptosis may occur if the injury is self-limited [18].

A conceptual framework of HSC activation delineates the response of the cell into two discrete phases: initiation and perpetuation (15) [14]. Initiation refers to early changes in gene expression and phenotype that enable the cells to respond to other cytokines and stimuli. Factors provoking initiation are largely derived from neighboring cells and include reactive oxygen species and specific matrix proteins (e.g., cellular fibronectin) derived from sinusoidal endothelium. Perpetuation results from the effects of these stimuli on maintaining the activated phenotype to generate scar. Perpetuation can be further subdivided into several discrete changes in cell behavior that include proliferation, contractility, fibrogenesis, matrix degradation, chemotaxis, retinoid loss, and leukocyte chemoattraction. As noted previously, it is important to recognize that the HSC is continuously evolving during progressive liver injured and fibrosis. Finally, resolution of HSC activation is increasingly appreciated and represents an essential step toward reversibility of fibrosis.

Proliferation

β-platelet-derived growth factor (β-PDGF) is the most potent and first stellate cell mitogen identified. Induction of β-PDGF receptors early in HSC activation confers responsiveness to this mitogen, which is minimally active toward quiescent stellate cells [19]. A host of other mitogens are also active toward stellate cells, including thrombin, vascular endothelial cell growth factor (VEGF), and fibroblast growth factor (FGF), among others [16].

Contractility

Contractility of HSCs may be a major determinant of increased portal resistance during liver fibrosis, though a role for HSC contracatility has not been established in normal liver blood flow regulation [20]. The major contractile stimulus toward HSCs is endothelin-1. Endothelin receptors are expressed on both quiescent and activated HSCs, but their subtype distribution changes from predominantly "A" to "B" isoform as cells activate, leading to altered cellular responses to this growth factor. Additionally, increased activation of proendothelin by endothelin-converting enzyme yields more active cytokine [21].

Fibrogenesis

Increased matrix production by activated HSCs occurs in response to fibrogenic mediators released during liver injury. The most potent stimulus to matrix production is transforming growth factor (TGF)-β1, which is derived from both paracrine and autocrine sources and has a complex and tightly regulated mechanism of activation to control availability of the active cytokine. A fibrogenic role has also been uncovered for connective tissue growth factor (CTGF), a TGF-β1-stimulated gene that stimulates matrix production by HSCs [22]. Additionally, leptin, a 16-kD hormone initially identified in adipose tissue, appears to be necessary for fibrogenesis because leptin-deficient animals lack the ability to accumulate scar following toxic liver injury [29, 24]. Interestingly, HSCs generate their own leptin and express signaling receptors for the hormone as they activate, providing the components of an autocrine loop. Fibrogenic actions of leptin may be particularly important in patients who are obese, because circulating leptin levels correlate closely with adipose mass and are significantly elevated in these individuals. Thus, elevated leptin levels may contribute to the fibrosis increasingly associated with fatty liver and NASH in obese patients.

Matrix Degradation

Quantitative and qualitative changes in matrix protease activity play an important role in ECM remodeling accompanying fibrosing liver injury and are largely orchestrated by HSCs [12]. In progressive fibrosis, the balance between matrix production and matrix degradation clearly favors production, through both increased fibrogenesis and inhibition of matrix degradation. A large family of matrix-metalloproteinases (MMP) has been characterized that specifically degrade collagens and noncollagenous substrates. In particular, HSCs are a key source of MMP-2, as well as stromelysin/MMP-3, both of which degrade constitutents of the normal subendothelial matrix and hasten its replacement by fibrillar collagen. Importantly, through the activation of tissue inhibitor of metalloproteinases-1 and -2 (TIMP-1 and -2), activated HSCs can also inhibit the activity of interstitial collagenases that degrade fibrillar collagen, thus favoring the accumulation of fibrillar matrix [26].

Chemotaxis

HSCs can migrate toward cytokine chemoattractants, an action that is characteristic of wound-infiltrating mesenchymal cells in other tissues as well. Chemotactic mediators include PDGF and monocyte chemoattractant protein-1 (MCP-1) [27, 28].

Retinoid Loss

As HSCs activate, they lose their characteristic perinuclear retinoid (vitamin A) droplets and acquire a more fibroblastic appearance. This pathway remains a somewhat mysterious aspect of HSC activation because it is unclear whether retinoid loss is required for HSC activation to proceed. If so, inhibitors of retinoid loss, once identified, might be used to antagonize HSC activation.

Leukocyte Chemoattractant and Cytokine Release

Increased production or activity of cytokines may be critical for both autocrine and paracrine perpetuation of HSC activation. Increasingly, it appears that all key cytokines acting upon activated HSCs are autocrine, suggesting that therapeutic efforts that antagonize HSC activation must reach the subendothelial milieu to be active. Additionally, HSCs can amplify the inflammatory response by inducing infiltration of mono- and polymorphonuclear leukocytes through release of chemoattractants.

Imatinib Mesylate

GLEEVEC™ is available in capsule or film coated tablet form and each form (capsule or tablet) contains imatinib mesylate equivalent to 100 mg or 400 mg of imatinib free base. Imatinib mesylate is designated chemically as 4-[(-phenyl]benzamide methanesulfonate and its structural formula is 4-Methyl-1-piperazinyl)methyl[-N-[4-methyl-3-[[4-(3-pyridinyl)-2-pyrimidinyl]amino]-phenyl]benzamide methanesulfonate.

Imatinib mesylate is a protein-tyrosine kinase inhibitor that inhibits the Bcr-Abl tyrosine kinase, the constitutive abnormal tyrosine kinase created by the Philadelphia chromosome abnormality in chronic myeloid leukemia (CML). It inhibits proliferation and induces apoptosis in Bcr-Abl positive cell lines as well as fresh leukemic cells from Philadelphia chromosome positive chronic myeloid leukemia. In colony formation assays using ex vivo peripheral blood and bone marrow samples, imatinib shows inhibition of Bcr-Abl positive colonies from CML patients.

In vivo, it inhibits tumor growth of Bcr-Abl transfected murine myeloid cells as well as Bcr-Abl positive leukemia lines derived from CML patients in blast crisis.

Imatinib is also an inhibitor of the receptor tyrosine kinases for platelet-derived growth factor (PDGF) and stem cell factor (SCF), c-kit, and inhibits PDGF- and SCF-mediated cellular events. In vitro, imatinib inhibits proliferation and induces apoptosis in gastrointestinal stromal tumor (GIST) cells, which express and activating c-kit mutation.

Amounts of GLEEVEC™ effective to treat hepatic fibrosis would broadly range between about 50 mg and about 600 mg per day and preferably between about 50 mg and about 200 mg per day administered orally. The rationale for this preferred dose range is based on FDA-approved GLEEVEC™ dosing for CML and gastrointestinal stromal tumors (GIST), which are 400 mg and 600 mg per day, respectively. Whereas treatment of CML and GIST require high doses of GLEEVEC™ in order for the drug to reach its targets (bone marrow and the tumor), the liver should be effectively targeted with lower doses because of relatively high concentrations of drug in liver following its oral administration and absorption in the intestine. These lower GLEEVEC™ doses should minimize the risk of toxicity both in liver and other organs. Since liver fibrosis is a disease resulting from chronic liver injury, treatment with GLEEVEC™ over a person's lifetime is envisioned, either alone or in conjunction with therapies aimed at eradicating or reducing the cause of chronic liver injury, for example with antiviral medications such as alpha interferon (Hoffman LaRoche, Nutley, NJ, Schering-Plough, Kenilswirth, NJ).

There is a huge potential economic impact of establishing a treatment for hepatic fibrosis. Currently there are over 4 million patients with chronic HCV infection in the United States (up to 1–2% of the population) and all are at risk for fibrosis and cirrhosis. Conservative estimates indicate that up to 100 million people may be infected worldwide. Moreover, chronic Hepatitis B, schistosomiasis, and immune diseases affect hundreds of millions more, particularly in the Far East and Africa. With steady advances in the understanding of hepatic fibrosis, the medical and patient communities are now anxiously awaiting progress in its treatment and are quite receptive to the prospect.

Currently there are no approved treatments for hepatic fibrosis in patients with chronic liver disease despite the rapidly accelerating worldwide morbidity from this disease. GLEEVEC™ has the unique advantages of a large amount of safety data already generated with excellent safety profile, and oral availability making delivery to the liver highly efficient and allowing the use of decreased doses that minimize toxicity. Moreover, a vast amount of pharmacokinetic and clinical information has been amassed for this drug.

The present invention is described below in examples which are intended to further describe the invention without limiting its scope.

EXAMPLES

Use of GLEEVEC™ as an Antifibrotic Therapy

Patients will be treated with GLEEVEC™ (imatinib mesylate) who have evidence of liver fibrosis (scarring) as seen on liver biopsy. Typically, these are patients with chronic Hepatitis C, Hepatitis B, autoimmune hepatitis, metabolic diseases or fatty liver and scarring seen with obesity, but any chronic liver disease associated with fibrosis will be an indication. Doses will range from 50 mg to 200 mg per day, with 100 mg per day as the median dose, administered orally. The efficacy of GLEEVEC™ treatment will be assessed using both non-invasive serologic testing of fibrosis markers in conjunction with liver biopsy at defined intervals (every 1–2 years) during therapy.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

References

1. Friedman, S. L.: Liver Fibrosis—From Bench to Bedside, *J. Hepatol.* 2003, 38 Supp. 1:38–53.

2. Kim, W. R.; Brown, R. S.; Jr., Terrault; N. A.; El-Serag, H.: Burden of Liver Disease in the United States: Summary of A Workshop. *Hepatology* 2002, 36:227–242.

3. Friedman, S. L.: Molecular Regulation of Hepatic Fibrosis, an Integrated Cellular Response to Tissue Injury. *J. Biol. Chem.*, 2000, 275:2247–2250.

4. Wong, L.; Yamasaki, G.; Johnson, R. J.; Friedman, S. L.: Induction of Beta-Platelet-Derived Growth Factor Receptor in Rat Hepatic Lipocytes During Cellular Activation *In Vivo* and In Culture; *J. Clin. Invest.*, 1994, 94:1563–1569.

5. Iredale, J. P.; Benyon, R. C.; Pikering, J.; McCullen, M.; Northrop, M.; Pawley, S.; Hovell, C. A; Arthur, M. J.: Mechanisms of Spontaneous Resolution of Rat Liver Fibrosis. Hepatic Stellate Cell Apoptosis and Reduced Hepatic Expression of Metalloproteinase Inhibitors, *J. Clin. Invest.*, 1998, 102:538–549.

6. Bonia, P. A.; Friedman, S. L.; Kaplan, M. M.: Is Liver Fibrosis Reversible? *N. Engl. J. Med.*, 2001, 344:452–454.

7. Druker, B. J.; Sawyers, C. L.; Kantarijian, H.; Resta, D. J.; Reese, S. F.; Ford, J. M.; Capdeville, R.; Talpaz, M.: Activity of A Specific Inhibitor of The BCR-ABL Tyrosine Kinase in The Blast Crisis of Chronic Myeloid Leukemia and Acute Lymphoblastic Leukemia with The Philadelphia Chromosome. *N. Engl. J. Med.*, 2001, 344:1038–1042.

8. Kantaijian, H.; Sawyers, C.; Hochhaus, A.; Guilhot, F.; Schiffer, C.; Gambacorti-Passerini, C.; Niederwieser, D.; Resta, D.; Capdeville, R.; Zoellner, U. et al.: Hematologic and Cytogenetic Responses to Imatinib Mesylate in Chronic Myelogenous Leukemia, *N. Engl. J. Med.*, 2002, 346:645–652.

9. Druker, B. J.; Talpaz, M.; Resta, D. J.; Peng, B.; Buchdunger, E.; Ford, J. M.; Lydon, N. B.; Kantaijian, H.; Capdeville, R.; Ohno-Jones, S. et al.: Efficacy and Safety of A Specific Inhibitor of The BCR-ABL Tyrosine Kinase in Chronic Myeloid Leukemia, *N. Engl. J. Med.,* 2001, 344: 1031–1037.

10. Apperley, J. F.; Gardembas, M.; Melo, J. V.; Russell-Jones, R.; Bain, B. J.; Baxter, E. J.; Chase, A.; Chessells, J. M.; Colombat, M.; Dearden, C. E. et al.: Response to Imatinib Mesylate in Patients with Chronic Myeloproliferative Diseases with Rearrangements of The Platelet-Derived Growth Factor Receptor Beta, *N. Engl. J. Med.,* 2002, 347:481–487.

11. Demetri, G. D.; von Mehren; M., Blanke; C. D., Van den Abeele, A. D.; Eisenberg, B., Roberts; P. J., Heinrich; M. C., Tuveson, D. A.; Singer, S.; Janicek, M. et al.: Efficacy and Safety of Imatinib Mesylate in Advanced Gastrointestinal Stromal Tumors, *N. Engl. J. Med.,* 2002, 347:472–480.

12. Manley, P. W.; Cowan-Jacob, S. W.; Buchdunger, E.; Fabbro, D.; Fendrich, G.; Furet, P.; Meyer, T.; Zimmermann, J.: Imatinib: A Selective Tyrosine Kinase Inhibitor, *Eur. J. Cancer,* 2002, 38 Suppl. 5:S19–27.

13. Kinnman, N., Francoz, C.; Barbu, V.; Wendum, D.; Rey, C.; Hultcrantz, R.; Poupon, R.; Housset, C.: The Myofibroblastic Conversion of Peribiliary Fibrogenic Cells Distinct from Hepatic Stellate Cells is Stimulated by Platelet-Derived Growth Factor During Liver Fibrogenesis. *Lab. Invest.,* 2003, 83:163–173.

14. Friedman, S. L.: Molecular Regulation of Hepatic Fibrosis: An Integrated Cellular Response to Tissue Injury, *J. Biol. Chem* 2000, 275:2247–2250.

15. Friedman, S. L.; Maher, J. J.; Bissell, D. M.: Mechanisms and Therapy of Hepatic Fibrosis: Report of The AASLD Single Topic Basic Research Conference.

16. Pinzani, M.; Marra, F.: Cytokine Receptors and Signaling During Stellar Cell Activation, *Semin. Liver Dis.* 2001, 21:397–416.

17. Bachem, M. G.; Schneider; E.; Gross, H.: Identification, Culture, and Characterization of Pancreatic Stellate Cells in Rats and Humans, *Gastroenterology* 1998, 115:421–432.

18. Iredale, J. P.: Stellate Cell Behavior During Resolution of Liver Injury, *Semin. Liver Dis.* 2001, 21:427–436.

19. Wong, L.; Yamasaki, G.; Johnson, R. J.; Friedman, S. L.: Induction of Beta-Platelet-Derived Growth Factor Receptor In Rat Hepatic Lipocytes During Cellular Activation *In Vivo* and in Culture, *J. Clin. Invest.* 1994, 94:1563–1569.

20. Rockey, D. C.: Hepatic Blood Flow Regulation by Stellate Cells in Normal and Injured Liver, *Semin. Liver Dis.* 2001, 21:337–350.

21. Shao, R.; Rockey, D. C.: Effects of Endothelins on Hepatic Stellate Cell Synthesis of Endothelin-1 During Hepatic Would Healing, *J. Cell Physiol.* 2002, 191:342–350.

22. Paradis, V.; Dargere, D.; Bonvoust, F.: Effects and Regulation of Connective Tissue Growth Factor on Hepatic Stellate Cells, *Lab Invest.* 2002, 82:767–774.

23. Saxena, N. K.; Ideda, K.; Rockey, D. C.: Leptin in Hepatic Fibrosis: Evidence for Increased Collagen Production in Stellate Cells and Lean Littermates of OB/OB/mice, *Hepatology* 2002, 35:762–771.

24. Ikejima, K.; Honda, H.; Yoshikawa, M.: Leptin Augments Inflammatory and Profibrogenic Responses in the Murine Liver Induced by Hepatotoxic Chemicals, *Hepatology* 2001, 34:288–297.

25. Benyon, D.; Arthur, M. J. P.: Extracellular Matrix Degradation and The Role of Stellate Cells, *Semin. Liver. Dis.* 2001, 21:373–384.

26. Iredale, J. P.: Tissue Inhibitors of Metalloproteinases in Liver Fibrosis, *Int. J. Biochem. Cell Biol.* 1997, 29:43–54.

27. Marra, F.; Romanelli, R. G.; Pastacaldi, S.: Monocyte Chemotactic Protein-1 as a Chemoattractant for Human Hepatic Stellate Cells, *Hepatology* 1999, 29:140–148.

28. Ikeda, K.; Wakahara, T.; Wang, Y. Q.: In Vitro Migratory Potential of Rat Quiescent Hepatic Stellate Cells and Its Augmentation by Cell Activation, *Hepatology* 1999, 29:1760–1767.

What is claimed is:

1. A method for treating hepatic fibrosis in a patient comprising administering to a patient in need of such treatment an effective amount to treat hepatic fibrosis of imatinib mesylate.

2. The method of claim 1 wherein said effective amount ranges between about 50 mg and about 600 mg imatinib mesylate per patient per day.

3. The method of claim 2 wherein said effective amount ranges between about 50 mg and about 200 mg imatinib mesylate per patient per day.

4. The method of claim 2 wherein imatinib mesylate is administered orally.

5. The method of claim 4 further comprising administering an antiviral medication.

* * * * *